United States Patent [19]

Lam et al.

[11] 4,251,660

[45] Feb. 17, 1981

[54] METHOD FOR PREPARING TETRAHYDROISOQUINOLINES

[75] Inventors: Bing L. Lam, Wynnewood; Wilford L. Mendelson, King of Prussia, both of Pa.; Charles B. Spainhour, Jr., Cherry Hill, N.J.

[73] Assignee: SmithKline Corporation, Philadelphia, Pa.

[21] Appl. No.: 932,586

[22] Filed: Aug. 10, 1978

[51] Int. Cl.³ .......................................... C07D 217/02
[52] U.S. Cl. .................................... 546/150; 564/384
[58] Field of Search ...................... 260/283 SY, 283 R; 546/150

[56] References Cited

U.S. PATENT DOCUMENTS

| 3,752,892 | 8/1973 | Hoegerle et al. | 260/239 BB |
| 3,947,456 | 3/1976 | Rheiner | 260/289 D |

OTHER PUBLICATIONS

Olah, Friedel Crafts Chemistry, Wiley, 1973, p. 262.
Deady et al., Chem. Comm., p. 799, (1971).

*Primary Examiner*—Jose Tovar
*Assistant Examiner*—D. B. Springer
*Attorney, Agent, or Firm*—William H. Edgerton; Richard D. Foggio; Alan D. Lourie

[57] ABSTRACT

A method for preparing 1,2,3,4-tetrahydroisoquinolines comprising heating N-halo or hydroxyethyl-N-benzylamines in an aluminum chloride melt at 160°–210°.

4 Claims, No Drawings

METHOD FOR PREPARING TETRAHYDROISOQUINOLINES

This invention relates to a new chemical method for preparing certain tetrahydroisoquinolines using an aluminum chloride melt with N-halo or hydroxyethylbenzylamines.

DESCRIPTION OF THE PRIOR ART

Certain substituted 1,2,3,4-tetrahydroisoquinolines have been described to be inhibitors of phenylethanolamine N-methyltransferase (U.S. Pat. No. 3,939,164). These compounds are described as prepared by hydrogenation of the corresponding isoquinolines.

A number of general synthetic methods for isoquinolines are reviewed in Organic Reactions, VI, Chapters 2, 3 and 4 several of which produce partially hydrogenated rings. A number of other aromatic compounds have been described as formed from various ring closures but most often with an activating group at the terminal carbon atom such as a phenyl or other branching group, Bull. Soc. Chem., France 1953 75, 1963 2292; Ann. Chem. 1973 1552; J. Heterocycl. Chem. 8 839 (1971); 11 8907 (1974); J. Med. Chem. 16 342 (1973).

Ring closure of 1-arylamino-3-phenyl or thienyl-3-alkanols using sulfuric acid to give aryl substituted tetrahydroquinolines was reported by V. N. Gogte et al., Tetrahydron Letters 39 3319 (1969).

In a series of articles S. W. Deady et al. have described the preparation of certain tetrahydroisoquinolines by heating N-bromoethylbenzylamines with aluminum chloride in decalin at temperatures of from 120°–155°; Aust. J. Chem. 26 2063 (1973); Chemical Communications 1971 799 and J. Chem. Soc. (C) 1973 782. To our knowledge this represents the sole cyclization of a non-activated halogen containing compound to prepare tetrahydroisoquinolines reported in the prior art.

Olah, *Friedel Crafts Chemistry*, Wiley 1973, page 262 described the use of aluminum chloride double salts with alkali metal halides in various Friedel Crafts alkylation procedures.

DESCRIPTION OF THE INVENTION

The chemical method of this invention is represented by the following reaction in its fundamental form.

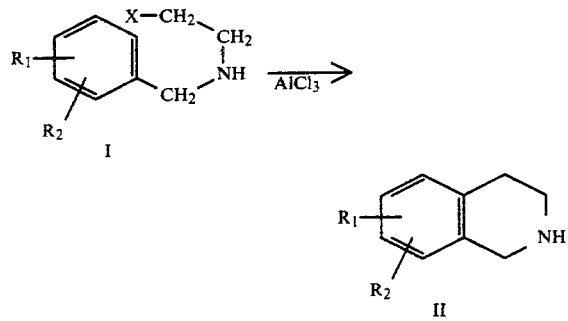

in which $R_1$ and $R_2$ are respectively hydrogen or chloro and X is hydroxy, chloro or bromo.

Preferably $R_1$ and $R_2$ are both chloro and are at the 7,8-positions. Also advantageously for the purpose of good yield X is chloro or hydroxy. For best advantage from the viewpoint of the overall cost of manufacture, X is hydroxy.

The benzylamine starting material (I) may be optionally used as the base or as an acid addition salt whose bulk at the nitrogen atom does not prevent cyclization or formation of the aluminum chloride complex necessary for cyclization. The hydrohalide salts, especially the hydrochloride, are preferred however any salt known to the art to be useful in synthetic reactions may be used. Examples of such salts are the sulfate, phosphate, sulfamate, methylsulfonate, acetate, maleate, nitrate, formate, oxalate and other common salts.

When the base is used it is converted to the hydrochloride salt in situ by the hydrogen chloride evolved during the reaction. Also other salts may be similarly converted to the hydrochloride during the reaction as will be evident to those skilled in the art.

The cyclization agent is aluminum chloride which forms a Friedel-Crafts complex with X which in turn cyclizes to form the desired product. Stoichiometric quantities of aluminum chloride may be used. In practice from 2 to 3 mole equivalents of aluminum chloride compared to the benzylamine are preferred. Excess amounts of the cyclization agent are not detrimental except for the added cost. When X is hydroxy an extra mole equivalent of aluminum chloride is necessary.

The aluminum chloride may also be admixed with other salts to control the temperature of the resulting eutectic mix or to assist reaction. Such are, most commonly, alkali metal or ammonium halides. Examples are ammonium chloride, sodium chloride or potassium chloride. These admixed salts are usually used in catalytic quantities, that is, in less than stoichiometric amounts based on the aluminum chloride. For other variations of the aluminum chloride reagent see Olah, *Friedel-Crafts Chemistry*, page 262. The preferred inorganic reactant is aluminum chloride-ammonium chloride.

The method of this invention is carried out by reacting the chosen benzylamine with the aluminum chloride salt mixture without an organic solvent at temperatures which maintain good contact between the reactants. In general the reaction times may run from about 160°–210° for from 5–18 hours. The time of reaction is of course dependent on temperature and will be until reaction is substantially complete. Very good yields are realized from a temperature range of about 180°–200° for 8–12 hours. When X is chloro or hydroxy and $R_1$ and $R_2$ are 7,8-dichloro, yields of about 80–85% are obtained using these conditions. There is a generation of hydrogen chloride during the reaction which must be trapped or vented as known to the art.

The reaction mixture is conveniently and optionally worked up by methods known to the art. Most commonly this involves quenching the reaction mixture, removal of the aluminum salts, then extraction and purification of the desired product.

The starting material (I) is prepared by N-alkylation of the ethanolamine such as using 2,3-dichlorobenzaldehyde under reductive conditions followed by thionylchloride treatment if the chloro derivative (I, X=Cl) is desired. The compounds of Formula I in which X is chloro or hydroxy and $R_1$ and $R_2$ are 7,8-dichloro are new compounds although certain position isomers are in the literature; J. Med. Chem. 10 692 (1967); U.S. Pat. No. 2,732,402; and J. Am. Chem. Soc. 76 2214 (1954).

The invention described above is both unexpected in view of the prior art and gives unusually good yields of the desired product. Deady et al. describe the cyclization by intramolecular condensation of a nonactivated bromo substituted on the primary carbon atom of the alkylene chain by heating at temperatures considerably under 150° in decalin in yields of 60-70%. Applicants and others in the art have found these yields not to be reproducible. The reaction often goes not at all or at most in about 30% yield. Considerable tarry by-products are obtained which along with the decalin solvent make the Deady process commercially of little advantage over the more standard hydrogenation method described in U.S. Pat. No. 3,939,164 due to the complicated workup of the reaction mixture.

Applicants by running the reaction neat with higher temperatures found that better more reproducable yields of the desired tetrahydroisoquinolines can be obtained with a process readily adaptable to commercial scale with a high throughput of product.

The claimed process in its preferred aspects in which $R_1$ and $R_2$ are 7,8-dichloro and X is chloro is even more unexpected since very little dehalogenation or randomization of halogen ring substitution was noted during the reaction. Substitution of a second ring halogen on the benzylamine starting material would also have been expected to make the cyclization more difficult.

The most advantageous aspect of this invention is the use of the terminal non-activated hydroxy group in the benzylamine starting starting material (I, X=OH). This variation of the invention eliminates the step of forming the halo but still gives very good yields. The prior art is, we believe, completely void of any such cyclization of a nonactivated primary alcohol.

The following examples are designed to teach the practice of this invention as well as its unexpected nature but not to limit its scope. All temperatures are on the Centigrade scale.

EXAMPLE 1

A solution of 1 kg (5.71 moles) of 2,3-dichlorobenzaldehyde in 7 l. of ethanol was prepared with stirring and heating. At room temperature 353.5 ml (5.85 moles) of ethanolamine was added dropwise. After allowing the reaction to proceed overnight, 278.7 g (7.37 moles) of sodium borohydride was added slowly with cooling over a three-hour period. The reaction mixture was stirred for 36 hours. The mixture was stripped to oil and extracted with 8 one liter portions of ethyl ether. The ether was washed with six 350 ml portions of 20% hydrochloric acid saturated with sodium chloride. The combined acid extracts were cooled to 0° and taken to pH 12 with solid sodium hydroxide then extracted with ethyl ether. The ethereal extracts were dried and stripped. After storage at 4° overnight the residue was taken into isopropanol-ether chilled and reacted with hydrogen chloride gas to separate white crystals of the desired hydroxyethylbenzylamine hydrochloride.

Calculated for: C, 41.77; H, 4.69; N, 5.54; Cl, 41.85. Found: C, 42.13; H, 4.71; N, 5.46; Cl, 41.46.

2,3-Dichlorobenzyl-N-hydroxyethylamine (50 g, 0.18 m) was mixed with 63 g (0.47 m) of aluminum chloride and 7.5 g (0.4 m) ammonium chloride. The mixture was heated with stirring to 195° (a melt was formed ~180°). After 1 hour a second portion of aluminum chloride (63 gm) was added to the reaction mixture and heating was continued for 7 hours keeping the reaction temperate 195°-200°. At the end of the reaction, the reaction was cooled to 80° and 75 ml of chlorobenzene was added to dilute the melt into a mobile liquid. Upon further cooling to 36°, the reaction mixture was poured into 1 liter of 10% hydrochloric acid. The solution was cooled and made basic with solid sodium hydroxide to pH 11 (by paper). Methylene chloride, 3×700 ml, was used to extract the basic aqueous phase. The combined organic phase was dried and concentrated to one-half of its original volume. Gaseous hydrogen chloride was then passed into the methylene chloride solution to precipitate crude product. The yield was 34.98 g (80.58%) crude 7,8-dichloro-1,2,3,4-tetrahydroisoquinoline hydrochloride which was 90.15% pure by high pressure liquid chromatographic analysis.

Alternatively, the same reaction was run with 100 g of benzylhydroxyethylamine and 2 portions of 126 g of aluminum chloride and one portion of 15 g of ammonium chloride between 185°-190° for 18 hours. Workup was identical to the above. The yield was 70.21 g (80.9%). The crude product was 88% pure by high pressure liquid chromatography.

EXAMPLE 2

Thionyl chloride (14.1 g, 0.118 m) was added slowly to a solution of 14.1 g (0.004 m) of N-hydroxyethyl-2,3-dichlorobenzylamine in 120 ml of chloroform. The mixture was heated at reflux for 3 hours with stirring, then cooled to 0°. The white product, 88.1% was N-2,3-dichlorobenzyl-N-chloroethylamine hydrochloride.

Calculated for: C, 38.80; H, 3.92; N, 5.05; Cl, 51.83. Found: C, 39.31; H, 4.03; N, 5.09; Cl, 51.57.

The N-2,3-dichlorobenzyl-N-chloroethylamine hydrochloride (4.0 g, 14.55 mm), ammonium chloride (0.3 g, 5.7 mm) and aluminum chloride (4 g, 30 mm) were mixed and placed in a cylindrical reactor with overhead stirring and immersed in an oil bath heated to 180°-185°. A slow evolution of gas occurred and the mixture formed a mobile dark solution. After 1.5 hours aluminum chloride (3 g, 22.5 mm) was added and the reaction continued for 16 hours. The reaction was cooled to 90° and poured into a rapidly stirred quench solution of cold dilute hydrochloride acid (25 ml of concentrated acid mixed with 75 ml of ice water). After stirring at room temperature the solution was nearly clear. The solution was cooled and treated with ammonium tartrate (10 g) and 50% sodium hydroxide solution. A precipitate of aluminum hydroxide formed transiently and dissolved as additional base was added to pH 12. The product was extracted into ethyl acetate and backwashed with brine. After drying over sodium sulfate, the product was stripped to a oil (2.8 g) which was dissolved in ether and treated with isopropanolic hydrogen chloride. The white solid which formed was stirred at 20° then filtered and washed with cold isopropanol, yield 2.82 g (11.82 mm, 81%); m.p. 221°-224° of 7,8-dichloro,2,3,4-tetrahydroisoquinoline hydrochloride which was 99% pure by gas chromatography.

EXAMPLE 3

(a) N-chloroethyl-2,3-dichlorobenzylamine (2.0 g, 7.3 mm), ammonium chloride (0.2, 3.7 mm) and aluminum chloride (2 g, 15 mm) were mixed and reacted as in Example 2 at 178°-183°. An acidic gas was evolved and the mixture formed a bright red melt. After 1.5 hours an additional 1.5 gm (11.25 mm) of aluminum chloride was added. More acidic gas was evolved. The reaction mixture was continued to be stirred for 16 hours. At end of this time flask contents as black melt were quickly poured into an ice cold solution of hydrochloric acid which was rapidly stirred (25 ml of conc. acid plus 75 ml of ice water). Resultant mixture was stirred rapidly until it reached room temperature. The clear light olive green solution then had 10 gm of ammonium tartrate dissolved in it. Solution was then titrated to pH 12 with solid sodium hydroxide (80%). The product was then extracted with 3×150 ml portions of ethyl ether and the light yellow organic layer dried over sodium sulfate and stripped to a deep gold or light brown oil of constant weight. The oil then was dissolved in 15 ml diethyl ether/10 ml isopropanol, chilled to 0° and hydrogen chloride bubbled into solution with good mixing until pH 2. A white precipitate started to form at about pH 4. The reaction mixture was then mixed for 15 minutes at 0° collected by filtration and washed with cold diethylether/isopropanol mixture. Yield of the desired 7,8-dichloro-1,2,3,4-tetrahydroisoquinoline hydrochloride was 1.50 g or 86.2% after drying overnight at 26° 760 mm. Thin layer chromatography showed the desired tetrahydroisoquinoline as the major component with only a trace of a faster running material.

(b) Using the same reaction conditions and methods of isolation N-hydroxyethyl-2,3-dichlorobenzylamine hydrobromide (2.0 g, 6.0 mm) was reacted in a melt of 5 g (37.5 mm) of aluminum chloride-0.3 g (5.6 mm) of ammonium chloride to give 1.19 g (75.3%) of 7,8-dichloro-1,2,3,4-tetrahydroisoquinoline hydrochloride which was 95.1% pure by high pressure liquid chromatography.

(c) A mixture of 2.9 g (7.8 mm) of the hydroxy hydrochloride salt gave 1.52 g (81.7%) of 98.7% pure product.

(d) A mixture of 4.0 g (11 mm) of N-bromoethy-2,3-dichlorobenzylamine hydrobromide (prepared by treating N-hydroxyethyl-2,3-dichlorobenzylamine with 48% hydrobromic acid at reflux for 12 hours), 9.6 g (72 mm) of aluminum chloride and 0.5 g (5.1 mm) of ammonia bromide was reacted as above at 167° with the aluminum chloride added 4 g at time 0; 3 g at 1 hour and 2.6 g at 3 hours to give 0.789 g (30.7%) of impure product as the hydrochloride salt.

(e) A mixture of 2.9 g (7.8 mm) of N-hydroxyethyl-2,3-dichlorobenzylamine hydrochloride, 5.0 g (37.5 mm) of aluminum chloride and 013 g (5.1 mm) of sodium chloride was reacted with the aluminum chloride added. 2 g at 0 time; 1 g at ½ hour and 2 g at 1¼ hour to give 1.57 g (81.7%) of 97.3% pure product by gas liquid chromatography.

(f) A mixture of 2.0 g (7.8 mm) of N-hydroxyethyl-2,3-dichlorobenzylamine hydrochloride and 5 g (37.5 mm) of aluminum chloride was reacted as above with the aluminum chloride additions at 0 time, 2 g; ½ hour, 1 g and 1¼ hour, 2 g to give 1.62 g (87.1%) of 7,8-dichloro-1,2,3,4-tetrahydroisoquinoline hydrochloride which is 97.93% pure by gas liquid chromatography.

EXAMPLE 4

(a) The reaction of Example 3 was run on a mixture of 2.0 g (7.8 mm) of N-hydroxyethyl-2,3-dichlorobenzylamine hydrochloride, 0.3 g (5.6 mm) of ammonium chloride and 5 g (37.5 mm) of aluminum chloride the latter of which was added 2 g at 0; 1 k g at ½ hour and 2 g at 1¼ hour at a temperature of 160° to give 1.6 g (86%) of 58.4% pure (gas liquid chromatography) product.

(b) The identical reaction run at 140° gave 1.54 g (82.8%) of unreacted starting material.

EXAMPLE 5

A solution of p-chlorobenzaldehyde (10 g, 0.071 m) and ethanolamine (4.88 g, 0.080 m) in methyl alcohol (90 ml) was stirred at room temperature for 30 hours. Sodium borohydride (4.9 g, 0.130 m) was added to the solution over 35 minutes as some foaming occurred. After one hour at room temperature the reaction was stripped in vacuo to a small volume, and water (100 ml) was added. The reaction was extracted with two portions of ether and the organic layer was backwashed with sodium chloride solution and dried over sodium sulfate. The solution was filtered and stripped to a small volume. Isopropanol (30 ml) was added and the solution cooled and stirred while a slow stream of hydrogen chloride was passed into the solution. The resulting N-hydroxyethyl-4-chlorobenzylamine hydrochloride was dried at 50°; m.p. 171°–172°; yield 11 g (70%).

$C_9H_{13}Cl_2NO$

Calculated: C, 48.67; H, 5.90; N, 6.31; Cl, 31.92. Found: C, 47.52; H, 5.77; N, 6.49; Cl, 31.87.

This compound was reacted with aluminum chloride-ammonium chloride at 160°–170° as in Example 1 to give 48% yield of 6-chloro-1,2,3,4-tetrahydroisoquinoline hydrochloride.

EXAMPLE 6

The preparation of the o-chloro starting material was carried out in the same way as that for the dichloro congener of Example 2 or the p-isomer of Example 5, Yield 14.20 g (90%), m.p. 155°–155.5°.

$C_9H_{13}Cl_2NO$

Calculated: C, 48.67; H, 5.90; N, 6.31; Cl, 31.92. Found: C, 48.76; H, 5.90; N, 6.16; Cl, 32.22.

A mixture of the amino alcohol (3.6 g, 16.2 mm) and sodium chloride 10.6 g, 10.2 mm) and aluminum chloride (4 g, 30 mm) was heated with stirring in an oil bath preheated to 170°. After ½ hour aluminum chloride (2 g, 15 mm) was added; after an additional ½ hour aluminum chloride (4.0 g, 30 mm) was added. After 16 hours the reaction was quenched by pouring into concentrated hydrochloric acid-ice mixture. The mixture was mixed at room temperature then filtered through super cell to remove black solids present. Sodium-potassium tartrate was added and the solution treated with sodium hydroxide solution (25%) to pH 13. The product was extracted into ether (dark layer) and the thin layer chromatogram showed three impurities in addition to the target compound, when compared with a reference material, prepared earlier. [Ethyl acetate: methanol:ammonium hydroxide-100:100:5, silica gel GF, visualized by iodoplatinate spray]. The ether layer was dried with sodium sulfate and stripped to a dark oil. The hydrochloride salt prepared in the usual manner (2.0 g, 60.5%) in ether:isopropanol contained three impurities seen earlier. The product, 8-chloro-1,2,3,4-tetrahydroisoquinoline hydrochloride, was crystallized from n-propanol:methanol for analysis, m.p. 235°–238°.

$C_9H_{11}Cl_2N$

Calculated for: C, 52.96; H, 5.43; N, 6.86; Cl, 34.74. Found: C, 52.74; H, 5.51; N, 6.94; Cl, 35.10.

EXAMPLE 7

A solution of 3,4-dichlorobenzaldehyde (10.0 g, 0.057 m) in absolute ethanol (90 ml) was treated with ethanolamine (3.9 g, 0.064 m) and stirred at ambient temperature for portionwise. The reaction foamed and the temperature rose to 55°. After 3 hours the reaction was stripped in vacuo and the product was extracted with three portions of ether. After drying with sodium sulfate, the ether was diluted with isopropanol and a slow stream of hydrogen chloride was passed into the solution. On standing in an icebox a white solid deposited. The product N-hydroxyethyl-3,4-dichlorobenzylamine hydrochloride, was dried at 50°, m.p. 144.5°-146°, yield 13.0 g (85.9%).

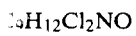

Calculated for: C, 42.13; H, 4.71; N, 5.46. Found: C, 42.07; H, 4.88; N, 5.56.

A mixture of the amino alcohol (4.0 g, 15.6 mm), ammonium chloride (0.6 g, 11.2 mm) and aluminuim chloride (4 g, 30 mm) were stirred at 183°-185°. After 0.5 hr add aluminum chloride (2 g, 15 mm) and after an additional 0.5 hr add aluminum chloride (4 g, 30 mm).

The reaction was continued for 18 hours and worked up by the method outlined in Example 6 to give 33.5% of 5,6-dichloro-1,2,3,4-tetrahydroisoquinolin hydrochloride and 32.9% of 6,7-dichloro-1,2,3,4-tetrahydroisoquinoline hydrochloride with a total of 2.43 g (65%).

EXAMPLE 8

The reactions of Examples 1 and 2 are repeated with equimolar quantities of N-hydroxyethylbenzylamine hydrochloride or N-chloroethylbenzylamine hydrochloride to give 1,2,3,4-tetrahydroisoquinoline. The use of N-chloroethyl-2,3-dichlorobenzylamine as the base gives good yields of 7,8-dichloro1,2,3,4-tetrahydroisoquinoline.

The attempted use of other dehydration or Friedel-Crafts catalysts such as sulfuric acid, ferric chloride or stannic chloride gave no cyclic product.

What is claimed is:

1. The method of preparing 7,8-dichloro-1,2,3,4-tetrahydroisoquinoline hydrochloride comprising the step of reacting N-hydroxyethyl-N-2,3-dichlorobenzylamine as the base or an acid addition salt thereof with aluminum chloride in the absence of an organic solvent at a temperature selected from the range of from about 160°-210° until the reaction is complete.

2. The method of claim 1 in which the N-hydroxyethyl-N-2,3-dichlorobenzylamine is in the form of the hydrochloride.

3. The method of claim 1 in which a catalytic quantity of an alkali metal or ammonium halide is added to the aluminum chloride.

4. The method of claims 1, 2 or 3 in which the reaction is carried out at a temperature selected from the range of from about 180°-200° for from 8-12 hours.

* * * * *

UNITED STATES PATENT AND TRADEMARK OFFICE
CERTIFICATE OF CORRECTION

PATENT NO. : 4,251,660

DATED : February 17, 1981

INVENTOR(S) : Bing L. Lam, Wilford L. Mendelson and Charles B. Spainhour, Jr.

It is certified that error appears in the above-identified patent and that said Letters Patent are hereby corrected as shown below:

Column 7, line 2, after "for" insert -- 24 hours. Sodium borohydride (3.4 g, 0.090 m) was added -- .

Signed and Sealed this

Fifth Day of May 1981

[SEAL]

Attest:

RENE D. TEGTMEYER

Attesting Officer

Acting Commissioner of Patents and Trademarks